US011668714B2

(12) United States Patent
Gilbert et al.

(10) Patent No.: US 11,668,714 B2
(45) Date of Patent: Jun. 6, 2023

(54) METHOD AND A SOLID SUPPORT FOR DETECTING TICK-BORNE MICROBES IN A BIOLOGICAL SAMPLE

(71) Applicant: Te?ted Oy, Jyväskylä (FI)

(72) Inventors: Leona Gilbert, Jyväskylä (FI); Kunal Garg, Jyväskylä (FI); Leena Meriläinen, Helsinki (FI); Kanoktip Puttaraksa, Jyväskylä (FI)

(73) Assignee: Te?ted Oy, Jyväskylä (FI)

( * ) Notice: Subject to any disclaimer, the term of this patent is extended or adjusted under 35 U.S.C. 154(b) by 0 days.

(21) Appl. No.: 17/752,277

(22) Filed: May 24, 2022

(65) Prior Publication Data

US 2022/0357323 A1    Nov. 10, 2022

Related U.S. Application Data

(62) Division of application No. 16/306,782, filed as application No. PCT/EP2017/060077 on Apr. 27, 2017, now Pat. No. 11,353,455.

(30) Foreign Application Priority Data

Jun. 3, 2016 (EP) .................... 16397518

(51) Int. Cl.
*A61K 39/002* (2006.01)
*G01N 33/53* (2006.01)
*G01N 33/569* (2006.01)

(52) U.S. Cl.
CPC ... *G01N 33/56911* (2013.01); *G01N 2333/20* (2013.01); *G01N 2469/20* (2013.01); *Y02A 50/30* (2018.01)

(58) Field of Classification Search
None
See application file for complete search history.

(56) References Cited

U.S. PATENT DOCUMENTS 6,013,460 A * 1/2000 Levin ............... G01N 33/56911
436/514

OTHER PUBLICATIONS

Merilainen, Leena, "Characterization and Immunological Aspects of Borrelia Burgdorferi Pleomorphic Round Bodies," Jyvaskyla Studies in Biological and Environmental Science, ISBN: 978-951-39-6335, Oct. 23, 2015, pp. 1-122.*
Merilainen, et al. (Microbiology, Mar. 2015, 161; 516-527).*
Miklossy, et al (J. Neuroinflammation, 2008, 5;1-18).*

* cited by examiner

*Primary Examiner* — Jennifer E Graser
(74) *Attorney, Agent, or Firm* — Ziegler IP Law Group LLC

(57) ABSTRACT

A solid support for detecting the presence of antibodies in a biological sample, where the solid support includes microbial antigens immobilized on the solid support, wherein the microbial antigens include at least one antigen prepared from the group consisting of pleomorphic round bodies of *Borrelia* genus, for example *Borrelia burgdorferi*, *Borrelia afzelii* and *Borrelia garinii*. Also, a method of detecting a tick-borne microbe in a biological sample, wherein the solid support is contacted with a biological sample.

8 Claims, 7 Drawing Sheets

Specification includes a Sequence Listing.

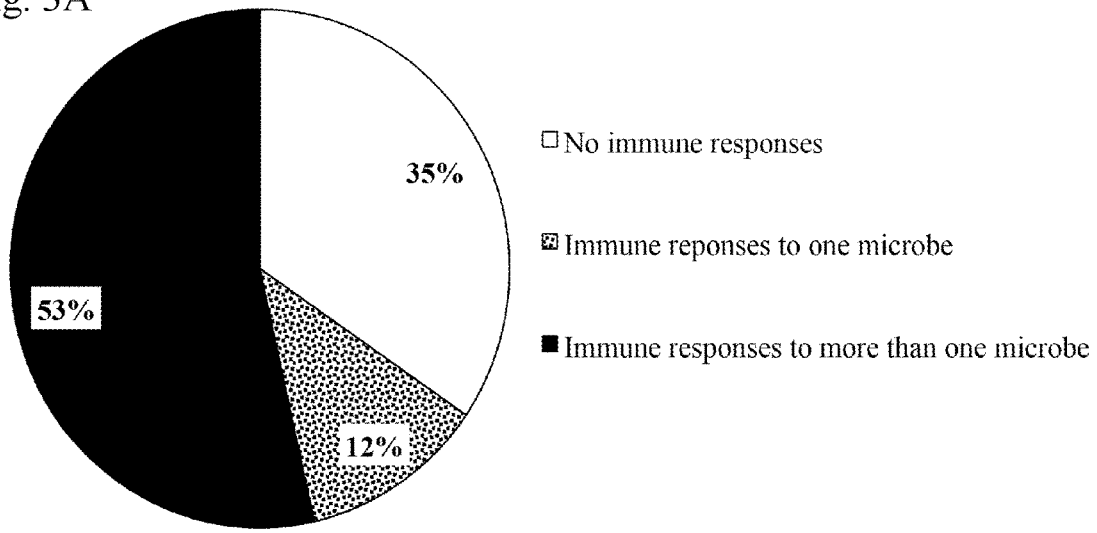
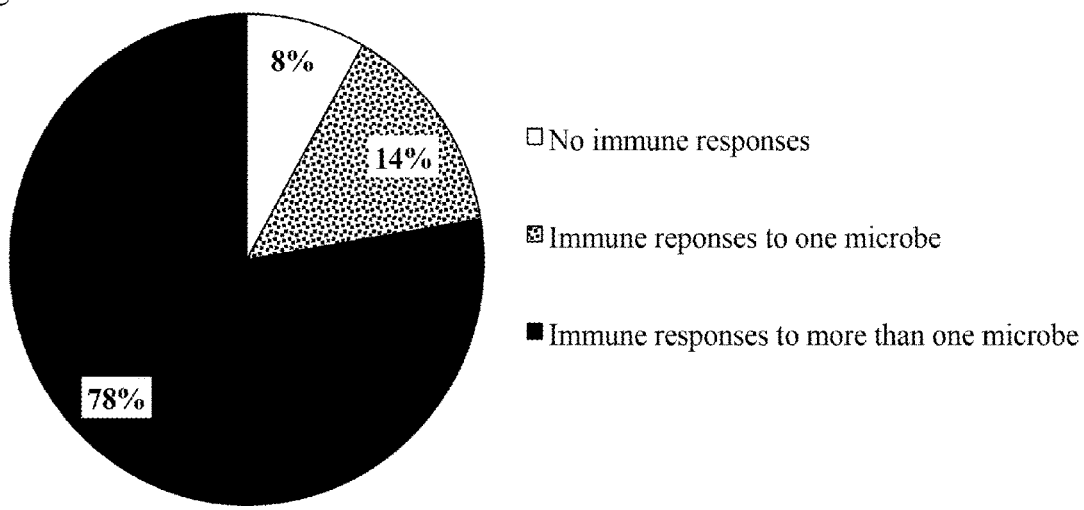

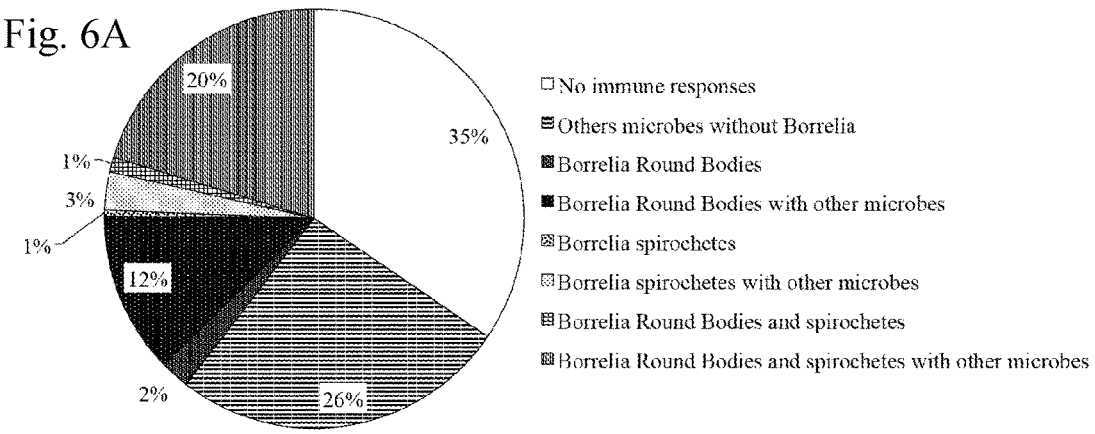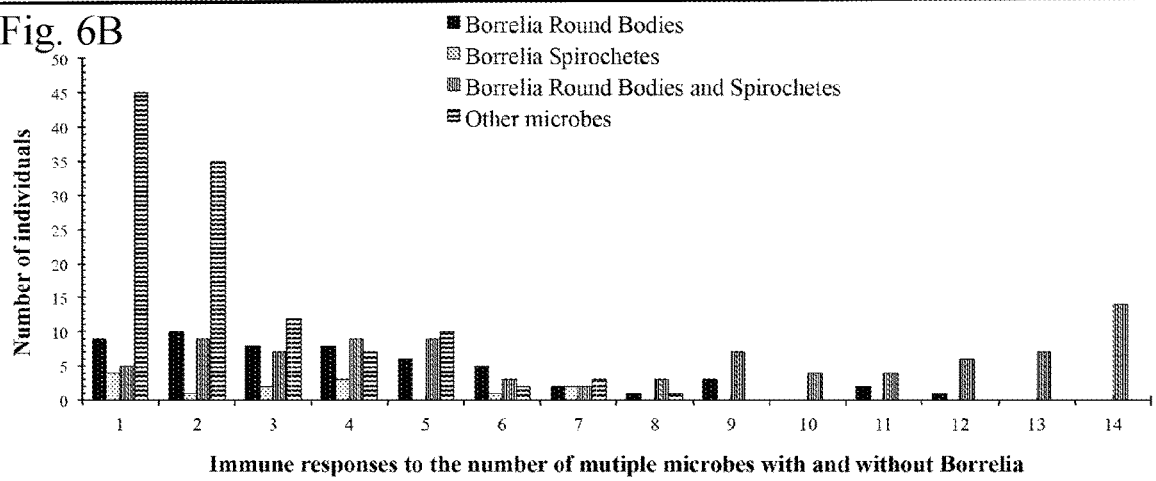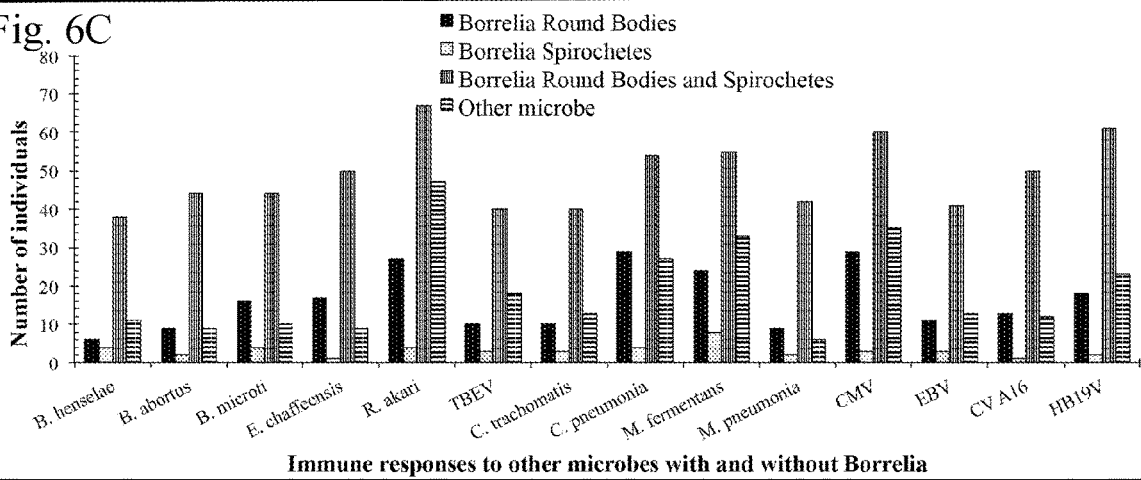

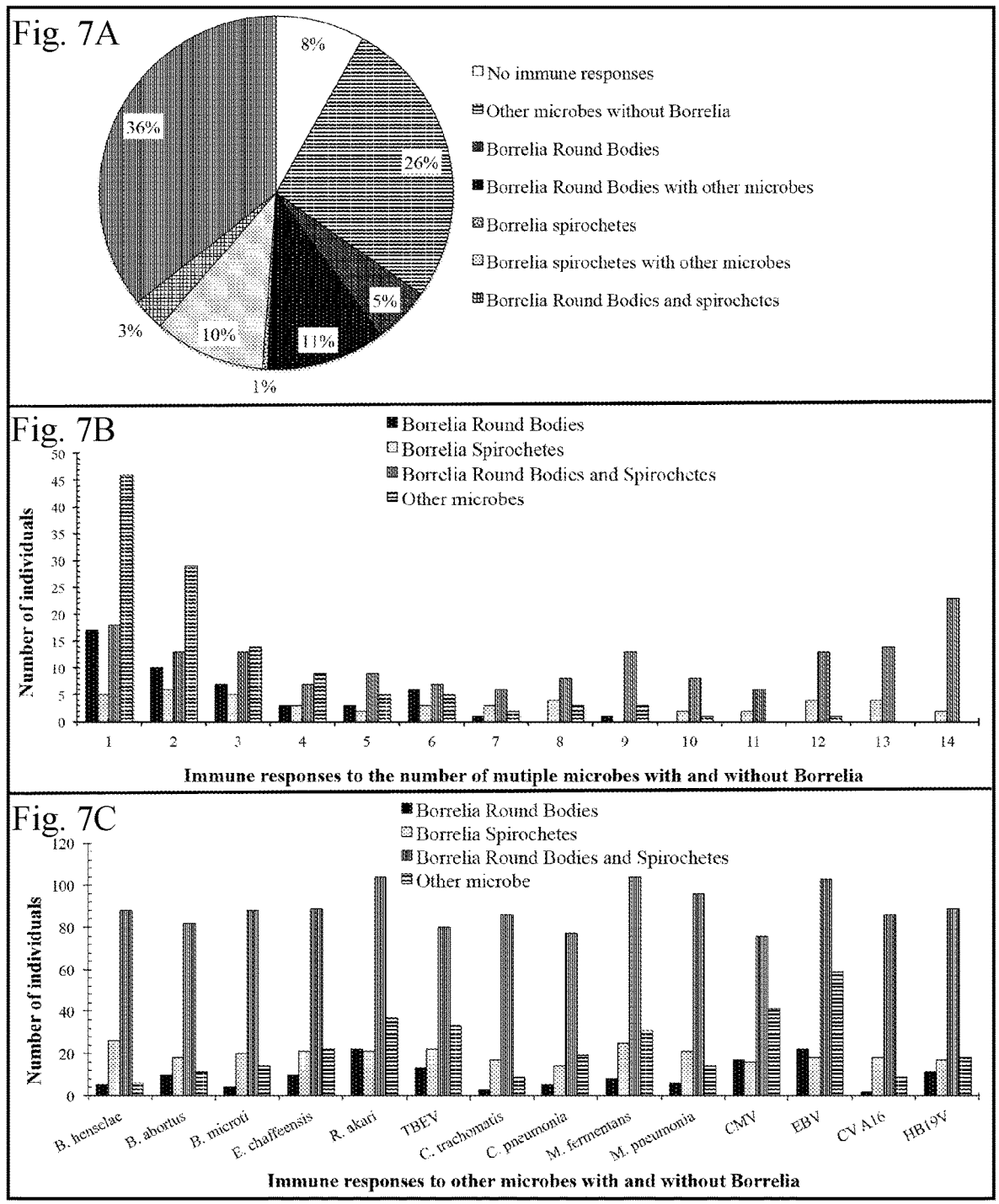

METHOD AND A SOLID SUPPORT FOR DETECTING TICK-BORNE MICROBES IN A BIOLOGICAL SAMPLE

INCORPORATION BY REFERENCE

The sequence listing in Text Document (.txt) format is incorporated herein by reference in its entirety.
 a. Name of File: 5209 SEQ.txt
 b. Date of Creation: 20 Mar. 2023
 c. Size of File: 4,547 Bytes

FIELD

The aspects of the disclosed embodiments relate to the detection of Lyme disease and other tick-borne diseases. The aspects of the disclosed embodiments also relate to the detection of antibodies in a biological sample. Particularly, the aspects of the disclosed embodiments provide a multiplex and multifunctional detection platform for Tick-borne disease (TBD) microbes

BACKGROUND

Tick-borne microbes (TBMs) are defined as macroscopic virulent entities that are spread to the host via a tick bite. Ticks are exceptional vectors for disease transmission and inhabit almost every continent, with the number of species worldwide topping 850. The most common tick-borne disease (TBD), both in Europe and North America, is Lyme disease caused by the spirochete *Borrelia* species[1,2]. Globally, Lyme disease is endemic in 80 countries including the 27 EU countries and central Asia[3,4]. Besides *Borrelia* there are many other bacteria and even viruses that co-infect such as *Babesia, Rickettsia, Ehrlichia, Bartonella,* Tick-borne encephalitis virus, etc[5,6]. The Center of Disease Control in the U.S.A and Europe has reported 300,000 and 85,000 annual TBD cases, respectively. However, the total number annual TBD cases are grossly underestimated as highlighted by the World Health Organization[7].

Clinical diagnosis of a presenting patient can be challenging since infections with TBMs initially manifest as a nonspecific febrile illness with or without specific organ system involvement, mimicking flu-like symptoms[2,5,8]. To further complicate treatment protocols, secondary infections with *Mycoplasma, Chlamydia,* Epstein-Barr virus or other viruses are common in these patients[6]. As a result of underestimation, misdiagnosis, co-infections and secondary infections, inadequate treatment can lead to development of severe clinical conditions such as fatigue, muscle/joint ache, cardiovascular/cognitive impairment, etc[9]. Patients develop severe clinical conditions as a result of inadequate diagnosis, and treatment results in diminishing their quality of life; consequently increasing healthcare burden[9,10]. Since clinical symptoms are diverse and unspecific, reliable diagnostics methods are paramount for timely and accurate treatment of patients[4,6,11,12].

The challenges in tick-borne infection diagnosis is that direct detection methods such as culturing and polymerase chain reaction (PCR) are difficult to conduct due to the low number of viable pathogens present in patient biopsies. This leads to negative results and do not exclude active infections or the different stages of disease that the patient might be suffering from[2,5,13]. Indirect methods such as Enzyme-linked Immunosorbent Assay (ELISA), is a limited antibody test that may have a weak or absent presence in early stages of the infection or disease. A remarkable number of false positive results, due to cross-reactivity issues among the different bacterial species also occur in these antibody-based assays. However, a positive specific antibody response may persist for months or years after successful treatment of the infection. These current methods fail to detect up to 80% of the first stage of tick-borne diseases and does not distinguish between acute and chronic infections[4,11]. To further add to the challenge, there are mostly ELISA based diagnostics for animals not humans that usually addresses one TBM and not multiple TBMs[3].

Ongoing diagnostic tools are not equipped with the current research findings. In recent years, scientific developments relating to *Borrelia* Round Bodies[14,] importance of *Borrelia* speciation[15,16,] polymicrobial infections[12], and IgM immune dysfunction[17] in TBD patients has challenged our clinical understanding about TBD. *Borrelia* round bodies are one of *Borrelia* spirochete's pleomorphic structure[14]. Over the years, pleomorphic forms of *Borrelia* have been labelled cell-wall deficient (CWD), L-forms, spheroplasts, protoplasts, propagules, or cysts[5,8,18-20]. Only recently, electron micrographs from Meriläinen et al. (2015) settled the discrepancy regarding *Borrelia's* pleomorphic morphology by concluding it to be a round body (RB). Meriläinen et al. (2015) induced *Borrelia* RB in human serum and demonstrated a spherical RB with intact yet flexible cell wall that was metabolically inactive with unique biochemical signatures. Although, clinical manifestations concerning *Borrelia's* pleomorphic morphology have been reported repeatedly, its pathogenic role in TBD has been debated and criticized. Ongoing diagnostic tools do not test TBD patients for *Borrelia* round body[8,21-25].

Current diagnostic tools may test for different *Borrelia* spirochetes, individually or collectively, as they present different clinical manifestations in individuals[16]. Recently, the multiplex TBD diagnostic tools can test for different recombinant *Borrelia* proteins, but TBD has been recognized as a polymicrobial infection disease, and ongoing diagnostic tools are unequipped to diagnose individuals for secondary opportunistic infections, co-infections, as well as auto-immune conditions associated with the infections[5,13,22-25].

To address pitfalls in ongoing TBD detection tools, the aspects of the disclosed embodiments provide a novel solid support comprising at least one immobilized antigen prepared from the group consisting of pleomorphic round bodies of *Borrelia* genus; for example, *Borrelia burgdorferi, Borrelia afzelii* and *Borrelia garinii*. The present results show for the first time that individual's immune system may specifically respond to only *Borrelia* round bodies and that this immune response may be related to persistent stage of Lyme disease.

SUMMARY

It is an aim of the aspects of the disclosed embodiments to provide a novel detection platform that outlines acute, past and particularly chronic or persistent stages of the TBDs the patient is experiencing. Additionally, the present specification may also address polymicrobial and immune dysfunction aspects associated with TBDs.

Thus, in one aspect the disclosed embodiments provide a solid support for detecting the presence of antibodies in a biological sample, said solid support comprising microbial antigens immobilized on said solid support, wherein said microbial antigens comprise at least one antigen prepared from the group consisting of pleomorphic round bodies of the species of *Borrelia* genus.

In another aspect, the disclosed embodiments provide a method of detecting a tick-borne microbe in a biological sample, the method comprising:
a. contacting a biological sample with a solid support comprising microbial antigens immobilized on said solid support in order to form a complex comprising a microbial antigen immobilized to said solid support and an antibody originating from said biological sample bound to said microbial antigen, wherein said microbial antigens comprise at least one antigen prepared from the group consisting of pleomorphic round bodies of the species of *Borrelia* genus;
b. detecting the presence of the complex obtained in step (a), wherein the presence of a complex comprising an antigen prepared from pleomorphic round bodies of at least one species of *Borrelia* genus is an indication of the presence of a tick-borne microbe in said biological sample.

In another aspect, the aspects of the disclosed embodiments provide a solid support as defined above for use in the diagnosis of Lyme disease.

In another aspect, the aspects of the disclosed embodiments provide a use of the solid support as defined herein for the manufacture of a diagnostic assay for the detection of a tick-borne microbe in a biological sample.

BRIEF DESCRIPTION OF THE DRAWINGS

In FIGS. 1A and 1B, abbreviations Bb, Ba, and Bg are *Borrelia burgdorferi* sensu stricto B31, *Borrelia afzelii* P12, and *Borrelia garinii* Fuji P1, respectively.

In FIGS. 2A and 3B, abbreviations Bb, Ba, and Bg are *Borrelia burgdorferi* sensu stricto B31, *Borrelia afzelii* P12, and *Borrelia garinii* Fuji P1, respectively.

Evaluation of (A) IgM (FIG. 3A) and (B) IgG (FIG. 3B) immune responses against one or multiple microbial antigens. An amount of 443 human sera were used to evaluate if individuals respond to only one microbial antigen or to multiple microbial antigens. Additionally, individuals with no immune response to 20 antigens were evaluated.

Figure 4:
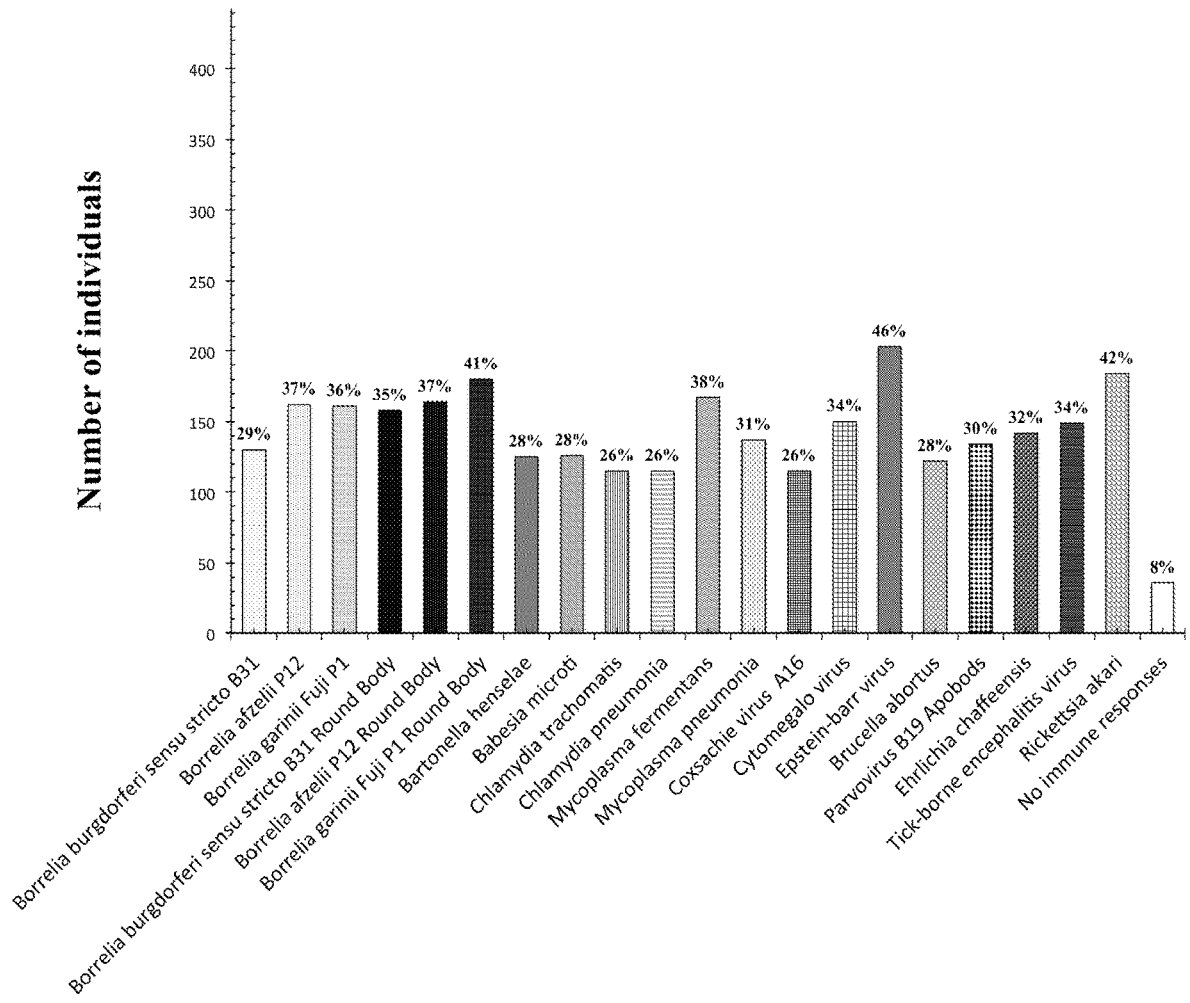

FIG. 4 IgG immune responses to individual microbial antigens. An amount of 443 human sera were used to evaluate the total number of immune responses to each microbial antigen utilized in this study. Additionally, individuals with no immune response to 20 antigens were evaluated.

Figure 5:
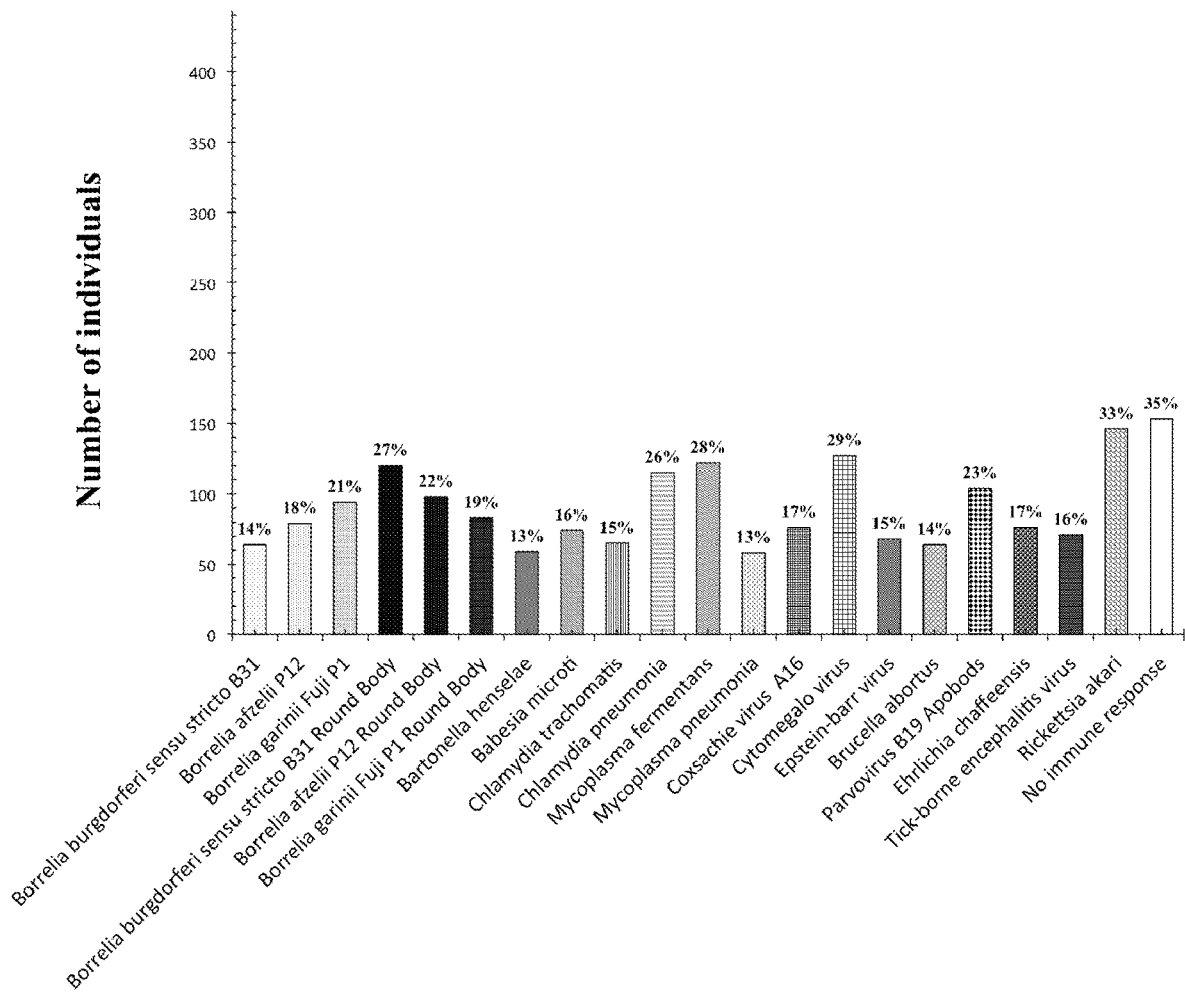

FIG. 5 IgM immune responses to individual microbial antigens. An amount of 443 human sera, were used to evaluate the total number of immune responses to each microbial antigen utilized in this study. Additionally, individuals with no immune response to 20 antigens were evaluated.

FIG. 6A Overall IgM immune response proportions by individuals to other microbes with and without *Borrelia*, FIG. 6B IgM immune responses by individuals to the number of multiple other microbes with and without *Borrelia*, and FIG. 6C IgM immune responses by individuals to specific other microbes with and without *Borrelia*. An amount of 443 human sera were used to compare the frequency of IgM immune responses to multiple other microbes and their specific types between individuals that responded to only *Borrelia* spirochetes, only *Borrelia* round bodies or a combination of *Borrelia* spirochete and round bodies. The term "other microbes" includes co-infections, secondary and auto-immune antigens such as *Bartonella henselae* (*B. henselae*), *Brucella abortus* (*B. abortus*), *Babesia microti* (*B. microti*), *Ehrlichia chaffeensis* (*E. chaffeensis*), *Rickettsia akari* (*R. akari*), Tick borne encephaltis virus (TBEV), *Chlamydia trachomatis* (*C. trachomatis*), *Chlamydia pneumonia* (*C. pneumonia*), *Mycoplasma fermentans* (*M. fermentans*), *Mycoplasma pneumonia* (*M. pneumonia*), Cytomegalo virus (CMV), Epstein-barr virus (EBV), Coxsachie virus A16 (CV A16), and Human Parvovirus B19 (HB19V).

FIG. 7A Overall IgG immune response proportions by individuals to other microbes with and without *Borrelia*, FIG. 7B IgG immune responses by individuals to the number of multiple other microbes with and without *Borrelia*, and FIG. 7C IgG immune responses by individuals to specific other microbes with and without *Borrelia*. An amount of 443 human sera were used to compare the frequency of IgG immune responses to multiple other microbes and their specific types between individuals that responded to only *Borrelia* spirochetes, only *Borrelia* round bodies or a combination of *Borrelia* spirochete and round bodies. The term "other microbes" includes co-infections, secondary and auto-immune antigens such as *Bartonella henselae* (*B. henselae*), *Brucella abortus* (*B. abortus*), *Babesia microti* (*B. microti*), *Ehrlichia chaffeensis* (*E. chaffeensis*), *Rickettsia akari* (*R. akari*), Tick borne encephaltis virus (TBEV), *Chlamydia trachomatis* (*C. trachomatis*), *Chlamydia pneumonia* (*C. pneumonia*), *Mycoplasma fermentans* (*M. fermentans*), *Mycoplasma pneumonia* (*M. pneumonia*), Cytomegalo virus (CMV), Epstein-barr virus (EBV), Coxsachie virus A16 (CV A16), and Human Parvovirus B19 (HB19V).

DESCRIPTION OF EMBODIMENTS

To date, the existing TBD diagnostic tools rely on screening one immune response (either IgG or IgM) for one disease, and often require a secondary confirmatory test for its findings. The present specification provides means and methods to detect chronic, latent or persistent stages of Lyme disease by detecting immune response against pleomorphic round bodies of the species of *Borrelia* genus.

At least 18 species of the *Borrelia* genus are known to cause Lyme disease or borreliosis and are transmitted by ticks[48]. The major Lyme disease pathogens are *Borrelia burgdorferi*, *Borrelia afzelii* and *Borrelia garinii*. Others are, for instance, *Borrelia miyamotoi*, *Borrelia tanukii*, *Borrelia turdi*, *Borrelia valaisiana*, *Borrelia carolinensis*, *Borrelia americana*, *Borrelia lusitaniae*, *Borrelia japonica*, and *Borrelia sinica*.

As a multiplex and multifunctional platform the present aspects can be used for diagnosing individuals against multiple microbes and antibody classes simultaneously. Microbial antigens that help in diagnosing primary, persistent, secondary, co-infection and auto-immune conditions in TBD individuals are listed below in Table 1.

The aspects of the disclosed embodiments are directed to a solid support for detecting the presence of antibodies in a biological sample, said solid support comprising microbial antigens immobilized on said solid support, wherein said microbial antigens comprise at least one antigen prepared from the group consisting of pleomorphic round bodies of the species of *Borrelia* genus, such as *Borrelia burgdorferi*, *Borrelia afzelii* and *Borrelia garinii*.

The term "pleomorphic" refers herein to pleomorphism, which in microbiology is defined as the ability of some bacteria to alter their shape or size in response to environmental conditions. The pleomorphic round bodies as defined in the present specification can be induced as disclosed in Meriläinen et al. (2015) or as disclosed in the Experimental Section below. Without wishing to be bound by theory, the basis behind barrel spirochete (i.e. long, corkscrew-shaped cells with mean length of 20 µm) changing its shape to pleomorphic round bodies (i.e. spherical cells with mean diameter of 2.8±0.46 µm) is that the bacterium is under physiological pressure from its environment. Therefore, in addition to changes to the media condition of the bacterium, stress conditions such as osmotic pressure also helps in inducing round bodies[47].

Previously, the round bodies (RBs) of *B. burgdorferi* have been ambiguously named in various ways. These terms include CWD and L-forms, spheroplasts, protoplasts, propagules and even cysts. Nonetheless, all of these labels describe the same spherical structures[14].

In an embodiment, the at least one antigen prepared from the group consisting of pleomorphic round bodies of a species of *Borrelia* genus is specific to pleomorphic round bodies of the species of *Borrelia* genus.

In an embodiment, the immobilized antigen on the solid support is a lysate or part of a lysate of cultured pleomorphic round bodies of *Borrelia* genus; for example, *Borrelia burgdorferi*, *Borrelia afzelii* or *Borrelia garinii*. Said immobilized antigen can also be a protein or peptide preparation of said pleomorphic round bodies. Other known preparations comprising antigens from microbial cells prepared, e.g., by the use of pH shift, human sera, salt concentration changes can also be used in the aspects of the disclosed embodiments.

In order to detect acute and chronic or persistent stages of Lyme disease simultaneously, said solid support may further comprise at least one immobilized antigen prepared from the group consisting of *Borrelia* genus, for example *Borrelia burgdorferi*, *Borrelia afzelii* and *Borrelia garinii*, in a native spirochete form or lysates thereof.

In an embodiment, the at least one immobilized antigen prepared from the group consisting of a species of *Borrelia* genus in a native spirochete form is specific to the species of the *Borrelia* genus in a native spirochete form.

In an embodiment, the assay is directed to the detection of one certain *Borrelia* species, for example, wherein 1) said solid support comprises an immobilized antigen prepared from pleomorphic round bodies of *Borrelia burgdorferi* and an immobilized antigen prepared from *Borrelia burgdorferi* in a native spirochete form; 2) said solid support comprises an immobilized antigen prepared from pleomorphic round bodies of *Borrelia afzelii* and an immobilized antigen prepared from *Borrelia afzelii* in a native spirochete form; or 3) said solid support comprises an immobilized antigen prepared from pleomorphic round bodies of *Borrelia garinii* and an immobilized antigen prepared from *Borrelia garinii* in a native spirochete form.

In an embodiment, the immobilized antigen prepared from pleomorphic round bodies of *Borrelia burgdorferi* is specific to pleomorphic round bodies of *Borrelia burgdorferi*, and athe immobilized antigen prepared from *Borrelia burgdorferi* in a native spirochete form is specific to *Borrelia burgdorferi* in a native spirochete form.

In an embodiment, the immobilized antigen prepared from pleomorphic round bodies of *Borrelia afzelii* is specific to pleomorphic round bodies of *Borrelia afzelii* and the immobilized antigen prepared from *Borrelia afzelii* in a native spirochete form is specific to *Borrelia afzelii* in a native spirochete form.

In an embodiment, the immobilized antigen prepared from pleomorphic round bodies of *Borrelia garinii* is specific to pleomorphic round bodies of *Borrelia garinii* and an immobilized antigen prepared from *Borrelia garinii* in a native spirochete form is specific to *Borrelia garinii* in a native spirochete form.

In an embodiment, the solid support is produced for a multiplex assay, wherein said solid support comprises immobilized antigens prepared from pleomorphic round bodies of a species of *Borrelia* genus, preferably *Borrelia burgdorferi*, *Borrelia afzelii* and/or *Borrelia garinii*. In a further embodiment, the multiplex assay comprises also immobilized antigens prepared from a species of *Borrelia* genus, such as *Borrelia burgdorferi*, *Borrelia afzelii* and/or *Borrelia garinii* in a native spirochete form.

In an embodiment, the immobilized antigens prepared from pleomorphic round bodies of *Borrelia burgdorferi*, *Borrelia afzelii* and *Borrelia garinii* are specific to pleomorphic round bodies of *Borrelia burgdorferi*, *Borrelia afzelii* and *Borrelia garinii*, respectively.

The multiplex assay may also comprise at least one immobilized antigen prepared from the group consisting of *Mycoplasma fermentans*, *Mycoplasma pneumonia*, *Bartonella henselae*, *Brucella abortus*, *Babesia microti*, *Chlamydia trachomatis*, *Chlamydia pneumonia*, *Ehrlichia chaffeensis*, Coxsackie virus A16, Epstein-barr virus (EBV), Cytomegalo virus (CMV), Human Parvovirus B19 Apobods, Tick-borne encephalitis virus (TBEV), and *Rickettsia akari*.

In an embodiment, the at least one immobilized antigen prepared from the group consisting of *Mycoplasma fermentans*, *Mycoplasma pneumonia*, *Bartonella henselae*, *Brucella abortus*, *Babesia microti*, *Chlamydia trachomatis*, *Chlamydia pneumonia*, *Ehrlichia chaffeensis*, Coxsackie virus A16, Epstein-barr virus, Cytomegalo virus, Human Parvovirus B19 Apobods, Tick-borne encephalitis virus, and *Rickettsia akari* is specific to *Mycoplasma fermentans*, *Mycoplasma pneumonia*, *Bartonella henselae*, *Brucella abortus*, *Babesia microti*, *Chlamydia trachomatis*, *Chlamydia pneumonia*, *Ehrlichia chaffeensis*, Coxsackie virus A16, Epstein-barr virus, Cytomegalo virus, Human Parvovirus B19 Apobods, Tick-borne encephalitis virus, and *Rickettsia akari*, respectively.

Said solid support may be made of glass or plastic, such as polystyrene or poly-propylene. Examples of solid support of the present specification are an antigen microarray or microwell plate. Antigen microarray is a form of protein microarray, which is also known as a protein chip. Microarray is a solid support (typically glass) on which thousands of different proteins (in this case antigens) are immobilized in discrete spatial locations, forming a high density protein dot matrix. Microwell plate is a flat plate with multiple "wells", where each well is used for one specific sample. The microwell plate is a standard tool in clinical diagnostic testing laboratories. A very common usage is in the enzyme-linked immunosorbent assay (ELISA).

In an embodiment, the present specification is directed to a solid support as defined herein for use in the diagnosis of Lyme disease, such as chronic/persistent Lyme disease.

In another embodiment, the present specification is directed to a use of the solid support as defined herein for the manufacture of a diagnostic assay for the detection of a tick-borne microbe in a biological sample. In an embodiment, said diagnostic assay is for the detection of Lyme disease in a patient, such as chronic/persistent Lyme disease in a patient.

The "patient", "individual" or "donor" may be a mammalian subject, such as a human subject.

The present specification is also directed to a method of detecting a tick-borne microbe in a biological sample, the method comprising:

(a) contacting a biological sample with a solid support comprising microbial antigens immobilized on said solid support in order to form a complex comprising a microbial antigen immobilized to said solid support and an antibody originating from said biological sample bound to said microbial antigen, wherein said microbial antigens comprise at least one antigen prepared from the group consisting of pleomorphic round bodies of a species of Borrelia genus; and (b) detecting the presence of the complex obtained in step (a), wherein the presence of a complex comprising an antigen prepared from pleomorphic round bodies of Borrelia genus, is an indication of the presence of a tick-borne microbe in said biological sample.

In an embodiment, the presence of the complex obtained in step (a) is detected by contacting said solid support with an anti-antibody reagent in order to form a complex of said microbial antigen, said antibody bound to said microbial antigen and said anti-antibody reagent.

The present specification also provides an opportunity to specifically and sensitively screen an individual's IgG and IgM or IgA response against multiple microbes in a single kit. Accordingly, said anti-antibody reagent may be anti-IgG antibody, anti-IgM antibody or anti-IgA antibody. For example, said anti-antibody reagent may be anti-human IgG antibody, anti-human IgM antibody or anti-human IgA antibody.

In an embodiment, said biological sample is a blood, serum, urine, saliva or tear sample, cerebrospinal fluid sample, or synovial fluid sample, such as a serum sample.

In an embodiment, the present method comprises a preceding step of culturing a species of Borrelia genus, such as Borrelia burgdorferi, Borrelia afzelii or Borrelia garinii, in conditions producing pleomorphic round bodies, performing lysis of the cultured cells, and coating or printing a solid support with the lysate or part of the lysate. Said conditions producing pleomorphic round bodies are as disclosed in Meriläinen et al. (2015) or as disclosed in the Experimental Section below, such as incubating Borrelia spirochete cells in distilled water or in changing salt concentrations, or in the presence of human sera or shifting the culture to acidic pH. After the culturing step, other known techniques for producing antigens from microbial cells can also be used in this aspect than cell lysis. For instance, antigenic peptides and proteins can be prepared from said pleomorphic round bodies for the coating or printing step.

Having now generally described the aspects of the disclosed embodiments, the same will be more readily understood by reference to the following Experimental Section, which is provided by way of illustration and is not intended as limiting.

Although methods and materials similar or equivalent to those described herein can be used in the practice or testing of the aspects of the disclosed embodiments, suitable methods and materials are described below.

Experimental Section
Materials and Methods
Ethical Approvals for Serum Sample Collection In total 532 human serum samples were collected from Borreliose Centrum Augsburg (BCA), Germany; King Christian 10th Hospital for Rheumatic Diseases, Denmark; and multiple clinics/specialty labs in the Europe that was approved by the Federal Institute for Drugs and Medical Devices, Germany (Ethical approval number: 95.10-5661-7066); Danish data protection agency and the regional ethics committee of Southern Denmark (Ethical approval number: S-20110029); and Western Institutional Review board (Ethical approval number: USMA201441), respectively. Of the 532 human serum samples, 51 negative controls were allotted to IgG and another 51 negative controls were allotted to IgM. The negative controls were utilized for establishing qualitative cut-off values for both antibody classes.

Preparation of Antigens for ELISA

All 532 human sera samples were tested against 20 microbial antigens for IgM and IgG antibody responses. In table 1, all 20 antigens have been enlisted. Borrelia spirochetes, Borrelia round bodies, and Human Parvovirus B19 Apobods were cultured and isolated in-house. Human Parvovirus B19 Apobods were cultured and isolated in accordance with the procedure reported elsewhere[26,27]. Dr. Marco Quevendo Diaz (Slovak Academy of Science) provided Rickettsia akari purified and deactivated lysates. Remaining 18 microbes were ordered as lyophilized microbial peptides from GeneCust. A stock solution of 1 mg/ml was prepared for Rickettsia akari and all microbial peptides to be directly utilized in ELISA.

Culturing and Isolation of Borrelia Species in Spirochete and Pleomorphic Forms

Borrelia cultures were obtained from the American Type Culture Collection (ATCC). Barbour-Stoenner-Kelly (BSK) medium was utilized for growing all three Borrelia cultures. The BSK medium was prepared in accordance with previously reported instructions[39]. In order to culture and isolate Borrelia species in their native spirochete form, each Borrelia strain was independently grown in BSK medium at 37° C. for 5-7 d. Post incubation, Borrelia cells were isolated by centrifuging culture tubes at 5000 g for 10 min. The supernatant was discarded, and the cell pellet was stored at −80° C. until further use[14].

For culturing different Borrelia round body strains, respective Borrelia spirochete cell pellets were resuspended in 2 ml of distilled water (ddH$_2$O). Borrelia spirochete cells were incubated in the water or in changing salt concentrations, or shifting to acidic pH or in the presence of human sera at 3° C. for 2 hrs. Post incubation, Borrelia cells were centrifuged at 5000 g for 10 min. The supernatant was discarded, and Borrelia round body pellet was stored at −80° C. until further use[14].

Culturing and Isolation of Human Parvovirus B19 Apobods:

Kivovich et al., (2010) and Thammasri et al., (2013) reported production of Human Parvovirus B19 (B19V) induced apoptotic bodies and isolation of of these apoptotic bodies herein called B19V Apobods. Briefly, B19V non-structural protein (NS1) was cloned together with enhanced green fluorescent protein (EGFP) in a modified pFastBacl vector. The modified pFastBacl vector was utilized to generate recombinant baculovirus in Autographa californica viral vector. The resulting structure was referred as AcCMV-EGFP-NS1. By using the Bac-to-Bac® Baculovirus Expression system, recombinant baculovirus stocks were prepared. A monolayer culture of insect cells Spodoptera frugiperda (Sf9 cells ATCCCRL-1711, Manassas, Va.) was utilized for viral stock amplification. The viral stocks contained recombinant bacmid DNA. Post infection (PI), 3 generations of viral stocks were collected, each at 48 or 72 h PI. After the cells were centrifuged and filtered, their transduction efficiency was determined by growth of HepG2 cells overnight and transduction with recombinant AcEGFP or AcEGFP-NS1. BD FACSCALIBUR flow cytometer (Becton-Dickinson, N.J., USA) was utilized to verify if viruses had 70% transduction efficiency for further use in the apoptotic body (ApoBods) induction. Further, HepG2 cells were transduced with third generation AcEGFP-NS1 viruses with a transduction efficiency of 70%. Finally, at 72 h post transduction, supernatant in the culture was centrifuged, pelleted, and stored at −80° C. until further use.

Processing Isolated Microbial Pellets for Utilization in ELISA

*Borrelia* spirochete, *Borrelia* round body, and B19V Apobods pellets were thawed on ice and resuspended in 100 µl of phosphate buffered saline solution (PBS, pH 7.4). To dissociate the in lysates, and homogenously dissolve the contents in PBS, all solutions in tandem were sonicated for 15 min (Bransoni C220), heated at 99.9° C. for 15 min and sonicated again for 15 min. Finally, 1 mg/ml stock concentration for all antigens was stored at +4° C.

ELISA Procedure

Antigen stock solutions (1 mg/ml) were diluted at 1:100 in 0.1 M carbonate buffer (0.1 M $Na_2CO_3$+0.1 M $NaHCO_3$, pH 9.5). Dilution volume was equally divided between stock solutions for microbes with two peptide sequences. Two positive controls, human IgG (Sigma) and human IgM (Sigma) were utilized in this study. Additionally, human IgG (Sigma) and human IgM (Sigma #18260) were interchangeably utilized as negative control for each other. The control stock solutions (1 mg/ml) were diluted at 1:100 in 0.1 M carbonate buffer. Positive and negative controls were utilized to maintain consistent optical density (OD) values at 450 nm.

A 100 µl of antigens and controls were coated in duplicates, on a flat bottom 96-well polystyrene ELISA plate (Nunc), and were incubated at +4° C. overnight. Post incubation, the plates were washed three times with 300 µl of PBS-Tween (PBS +0.05% Tween 20) and were then coated with a 100 µl of 2% BSA (Sigma #A7030) in PBS. After an overnight incubation at +4° C., the 2% BSA in PBS was discarded. Further, 100 µl of patient serum diluted at 1:200 in 1% BSA/PBS was added. The plates were then allowed to incubate for 2 hrs at room temperature (RT). Post incubation, the plates were washed five times with 300 µl of PBS-Tween. An amount of 100 µl of Horse Radish Peroxidase (HRP) conjugated to mouse anti-human IgG (Abcam) or rabbit anti-human IgM (Antibodies Online) was introduced to the plates at 1:10000 or 1:1000 dilution factor, respectively. After 1.5 hrs incubation at RT, the plates were washed five times with 300 µl of PBS-Tween and were then supplemented with 100 µl of 3,3',5,5' Tetramethylbenzidine substrate (TMB, 1-Step ultra TMB-ELISA substrate, Thermo-Piercenet #34028). Plates that were previously supplemented with HRP conjugated to mouse anti-human IgG or IgM, were incubated at RT for 5 min or 1 h, respectively. The reaction between the secondary antibodies and TMB substrate was stopped by adding 100 µl of 2 M $H_2SO_4$. Further, Victor™ $X^4$ multi-label plate reader (Perkin Elmer 2030 manger) was utilized to measure the OD values at 450 nm at 0.1 sec.

Data Processing

For quality assurance purpose, each duplicate was assessed to be present within 30% range of each other. Instead of assessing duplicates to be present within 30% of their mean[40], duplicates were assessed to be present within 30% range of each other. Since duplicates within 30% range of each other are independent of their mean, difference between the readings is highly limited when compared to duplicates within 30% of their mean. A set of 51 negative controls was utilized in IgG and another set of 51 negative controls was utilized in IgM to establish qualitative cut-off values for 20 antigens. For an antigen, the cut off value was established by adding mean of all average O.D values to three times the standard deviation of all average OD values[41]. On establishing cut-off values for 20 antigens, all average OD values were divided with their respective antigen cut-off values to normalize the dataset. By normalizing all OD values, an optical density index (ODI) dataset was established for both antibody types. Finally, the ODI values were converted into a binary data set that contained 1 or 0 to denote positives or negative, respectively.

The variation was assessed from calculating intra- and inter-assay variation[42]. Intra-assay variation was determined by the duplicate measurements from one high titer and one low titer sample on the same plate. For inter-assay variation, the variation was determined by measuring six high titer samples and six low titer samples from different plates that were performed on different days by different operators.

Equipment Utilized

ND 1000 spectrophotometer (Finnzymes) was used to measure protein concentration of cell lysates at 280 nm. Victor™ $X^4$ multi-label plate reader (Perkin Elmer 2030 manger) was utilized to measure the OD values at 450 nm at 0.1 sec. Microplate washer DNX-9620G (Nanjing Perlove Medical Equipment Co., Ltd) was used for washing ELISA microplates.

Results

FIGS. 1A, 1B, 1C, 2A, 2B and 2C demonstrate immune responses by 443 individuals to a combination of *Borrelia* spirochetes and round bodies, only *Borrelia* spirochetes, and only *Borrelia* round bodies. The total number of IgM and IgG (FIGS. 1A and 2A) immune responses to only *Borrelia* round bodies is consistently higher when compared the total number of IgM and IgG immune responses to only *Borrelia* spirochetes. Also, the total number of IgM and IgG (FIGS. 1A and 2A) immune responses to different combinations of *Borrelia* spirochetes and round bodies is higher when compared to the total number of IgM and IgG immune responses to only *Borrelia* spirochetes and only *Borrelia* round bodies. Further, in FIGS. 1B and 2B, different species of *Borrelia* spirochete witnessed a higher number of immune responses when compared to the total number of immune responses recorded for different combinations of *Borrelia* spirochetes. Similarly, in FIGS. 1C and 2C, higher number of immune responses was recorded for different species of *Borrelia* round bodies when compared to different combinations of *Borrelia* round bodies. FIGS. 1A, 1B, 1C, 2A, 2B and 2C suggest that in addition to different species of *Borrelia* spirochetes, different species of *Borrelia* round bodies may help in tremendously improving the efficiency of diagnostic tools to detect a *Borrelia* infection in individuals.

Figure 1A:
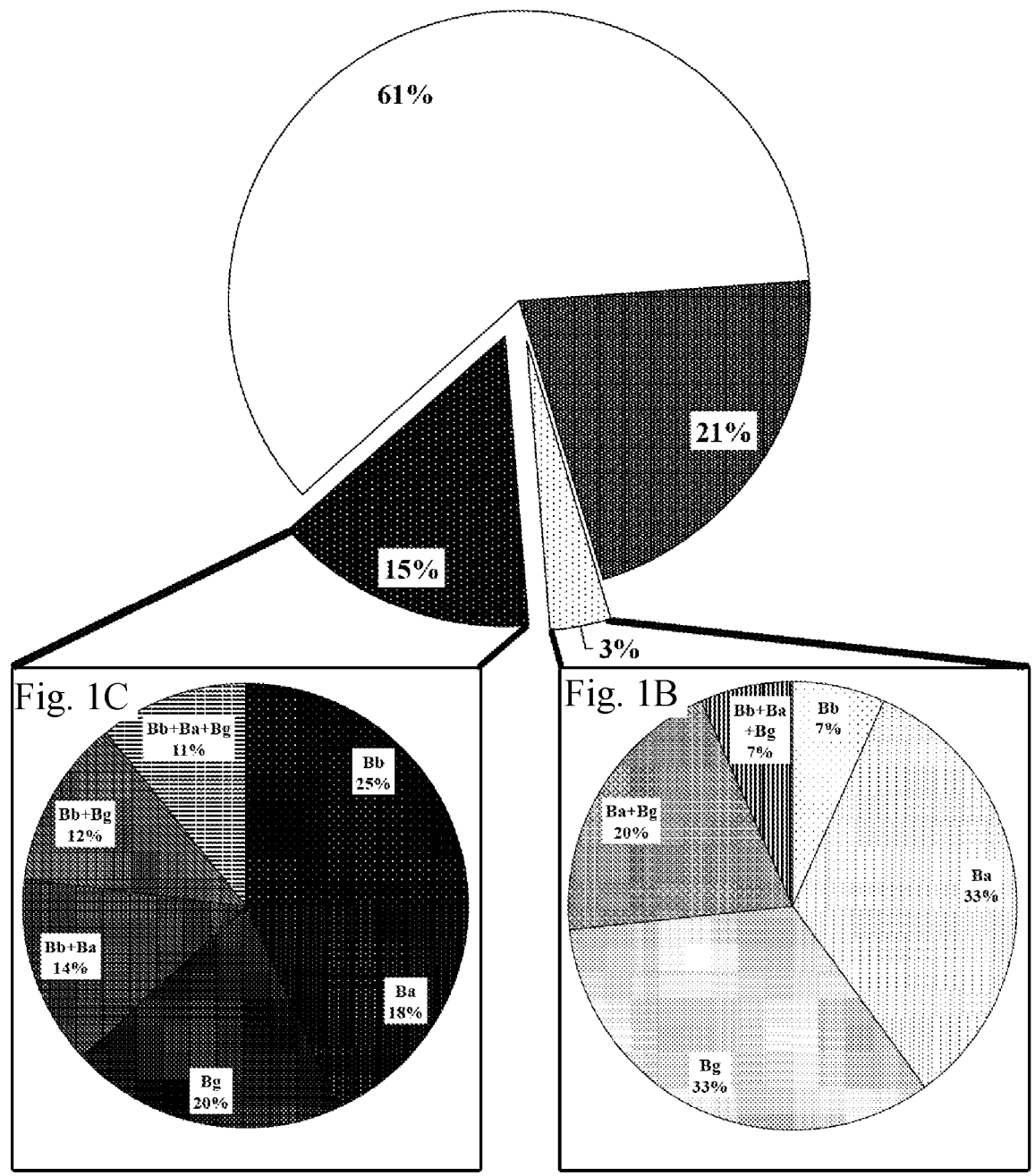
FIG. 1A Overall IgM immune responses to all *Borrelia* antigens, FIG. 1B only *Borrelia* spirochetes, and FIG. 1C only *Borrelia* round bodies.

In FIG. 1A, 95 (21%), 15 (3%), and 65 (15%) individuals with IgM responded to *Borrelia* spirochetes and round bodies, only *Borrelia* spirochetes, and only *Borrelia* round bodies, respectively. The total number of immune responses to only *Borrelia* round body was about 5 fold greater when compared to the total number of immune responses to only Borrelia spirochetes. Remaining 268 (61%) individuals did not respond to any Borrelia antigens. Borrelia round body represents dormant or latent form[5,9,14] of the native Borrelia spirochete structure. Patients responding to the Borrelia round body more than its own spirochete structure with an IgM suggests IgM immune dysfunction[17]. Similarly, in FIG. 2A, 171 (38%), 47 (11%), and 71 (16%) individuals with IgG responded to Borrelia spirochetes and round bodies, only Borrelia spirochetes, and only Borrelia round bodies, respectively. The total number of immune responses to only Borrelia round body was approximately 2 fold greater when compared to the total number of immune responses to only Borrelia spirochetes. Remaining 154 (35%) individuals did not respond to any Borrelia antigens. Higher number of immune responses to Borrelia round body suggests that a diagnostic kit with only Borrelia spirochetes cannot offer individuals a complete and reliable diagnosis for a Borrelia infection. Hence, implementation of Borrelia round bodies alongside Borrelia spirochetes for diagnosing TBD patients is an absolute novelty from this study.

Individuals infected with different strains of Borrelia require different therapeutic treatments[16]. Thus, individuals must be diagnosed for different Borrelia strains. Immune responses to only Borrelia spirochetes and only Borrelia round bodies (FIGS. 1A and 2A) were further speciated (in FIGS. 1B, 1C, 2B, and 2C) to evaluate if the total number of immune responses to individual Borrelia strains exceeds the total number of immune responses to different combinations of Borrelia strains. The total number of immune responses to individual Borrelia strains was consistently higher when compared with the total number of immune responses to different combinations of Borrelia strains (FIGS. 1B, 1C, 2B, and 2C).

Figure 2A:
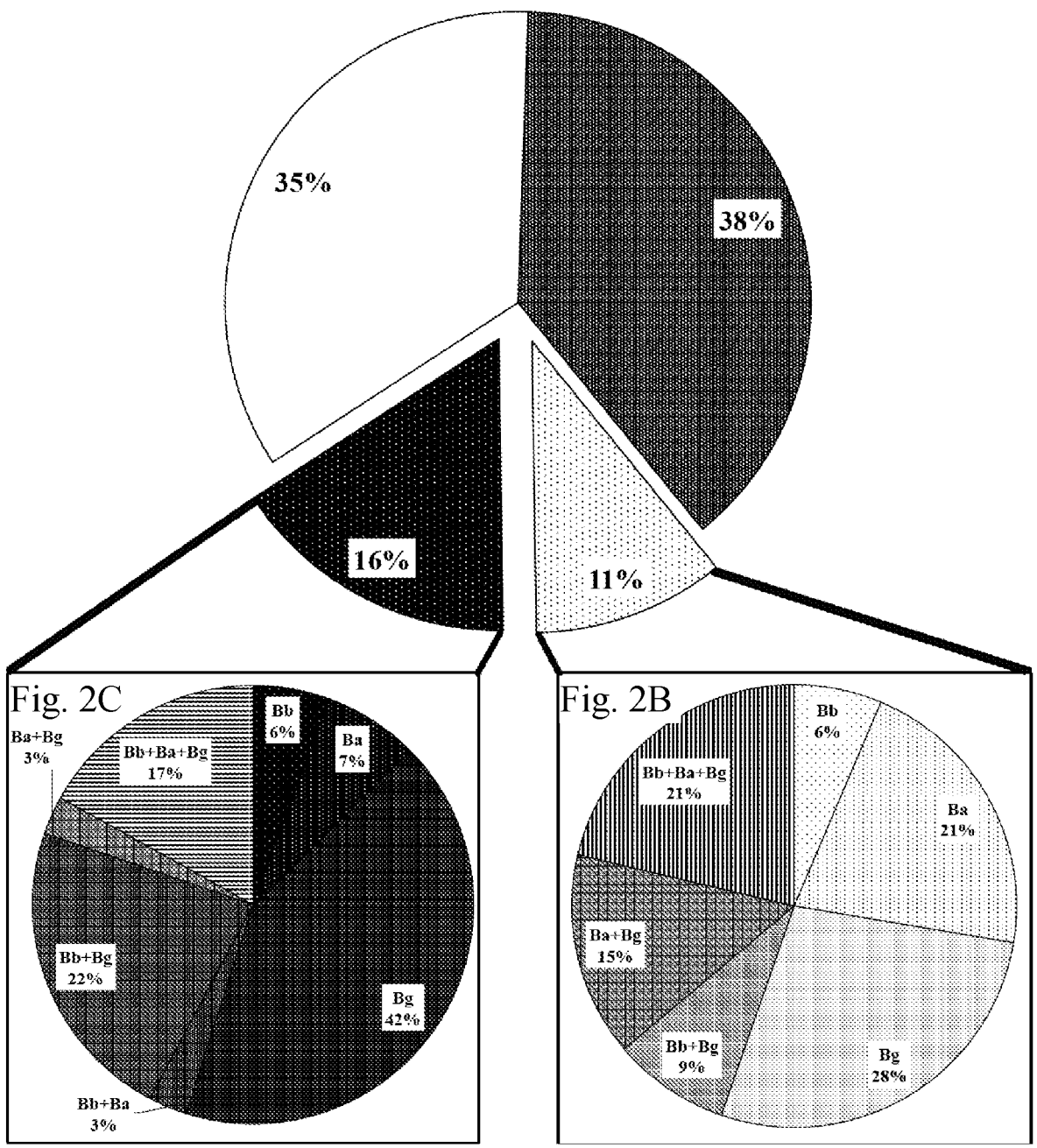
FIG. 2A Overall IgG immune responses to all *Borrelia* antigens, FIG. 2B only *Borrelia* spirochetes, and FIG. 2C only *Borrelia* round bodies.

In FIG. 1A, 15 (3%) individuals that responded to only Borrelia spirochetes were further speciated and evaluated in FIG. 1B. Of the 15 (3%) individuals, 1 (7%), 5 (33%), and 5 (33%) individuals responded to Borrelia burgdorferi (Bb), Borrelia afzeilii (Ba), and Borrelia garinii (Bg) spirochetes, respectively. Further, 3 (20%), and 1 (7%) individual responded to a combination of Ba+Bg, and Bb+Ba+Bg spirochetes, respectively. Of the 15 individuals, 4 (27%) individuals responded to a combination of different Borrelia strains, whereas 11 (73%) individuals responded to different Borrelia strains. Similarly, in FIG. 2A, 47 (11%) individuals that responded to only Borrelia spirochetes were further speciated and evaluated in FIG. 2B. Of the 47 (11%) individuals, 3 (6%), 10 (21%), and 13 (28%) individuals responded to Bb, Ba, and Bg spirochetes, respectively. Further, 4 (9%), 7 (15%), and 10 (21%) individuals responded to a combination of Bb+Bg, Ba+Bg, and Bb+Ba+Bg spirochetes, respectively. Of the 47 (11%) individuals, 21 (45%) individuals responded to a combination of different Borrelia strains, whereas 26 (55%) individuals responded to different Borrelia strains. No immune responses were recorded for Bb+Ba combination in both IgM (FIG. 1B) and IgG (FIG. 2B). Also, in FIG. 1B no immune responses were recorded for Bb+Bg combination.

In FIG. 1A, 65 (15%) individuals that responded to only Borrelia round bodies were further speciated and evaluated in FIG. 1C. Of the 65 (15%) individuals, 16 (25%), 12 (18%), and 13 (20%) individuals responded to Bb, Ba, and Bg round bodies, respectively. Further, 9 (14%), 8 (12%), and 7 (11%) individuals responded to a combination of Bb+Ba, Bb+Bg, and Bb+Ba+Bg round bodies, respectively. Of the 65 (15%) individuals, 24 (37%) individuals responded to a combination of different Borrelia strains, whereas 41 (63%) individuals responded to different Borrelia strains. Similarly, in FIG. 2A, 71 (16%) individuals that responded to only Borrelia round bodies were further speciated and evaluated in FIG. 2C. Of the 71 individuals, 4 (6%), 5 (7%), and 30 (42%) individuals responded to Bb, Ba, and Bg round bodies, respectively. Further, 2 (3%), 16 (22%), 2 (3%), and 12 (17%) individuals responded to a combination of Bb+Ba, Bb+Bg, Ba+Bg, and Bb+Ba+Bg round bodies, respectively. Of the 71 individuals, 32 (45%) individuals responded to a combination of different Borrelia strains, whereas 39 (55%) individuals responded to different Borrelia strains. No immune responses were recorded for Ba+Bg combination in both IgM (FIG. 1C) and IgG (FIG. 2C). Clearly, the total number of immune responses to individual Borrelia strains exceeds the total number of immune responses to Borrelia strains in combinations (in FIGS. 1B, 1C, 2B, and 2C). Higher number of immune responses to individual Borrelia strains suggests prevalence of distinct epitopes between different Borrelia strains[43]. Excluding different Borrelia strains from a diagnostic tool may limit its sensitivity[44].

FIGS. 3A and 3B presents IgM (FIG. 3A) and IgG (FIG. 3B) immune responses from 443 individuals to one or multiple microbial antigens and evaluates relevance of polymicrobial conditions in TBD. Globally, the medical community and diagnostic industry have recognized polymicrobial infections in numerous diseases such as measles, tuberculosis, hepatitis, acquired immune deficiency syndrome (AIDS), and other[12,45]. However, the TBD diagnostic landscape concerning polymicrobial infections had not changed[46]. In FIG. 3A, 237 (53%) individuals responded to multiple microbial antigens whereas 53 (12%) individuals responded to any single microbial antigen. Likewise, FIG. 3B determined that 344 (78%) individuals responded to multiple microbial antigens whereas 63 (14%) individuals responded to any single microbial antigen. Experimental evidences regarding polymicrobial infections in TBD from FIGS. 3A, 3B and 3C advocates an imperative paradigm shift in the field of TBD diagnostics. Remaining 153 (35%) and 36 (8%) individuals did not produce an immune to microbial antigens when tested for IgM and IgG, respectively. Individuals responding to multiple microbes with IgM (FIG. 3A) are about 5 fold greater when compared to individuals responding to a single microbe. Similarly, in FIG. 3B, individuals responding to multiple microbes are about 6 fold greater when compared to individuals responding to a single microbe. Response to multiple antigens (53%) with an IgM (FIG. 3A) suggests that immune dysfunction could be a common phenomenon among TBD individuals[17]. Moreover, FIGS. 3A and 3B suggest that polymicrobial infections may be a more common phenomenon to be observed with IgG than IgM.

FIGS. 4 and 5 present IgM and IgG immune responses to individual microbial antigens, respectively. The total number of immune responses to each individual antigen was consistently higher in IgG when compared to IgM. Immune responses to Borrelia round bodies were either higher or similar when compared to their respective spirochete strains. Equivalent number of immune to Borrelia round bodies in comparison to Borrelia spirochetes suggests that Borrelia round bodies may help in maximizing sensitivity of Borrelia diagnostic tools. An amount of 130 (29%) and 64 (14%) individuals responded to Borrelia burgdorferi sensu stricto B31 for IgG and IgM, respectively; 162 (37%) and 79 (18%) individuals responded to Borrelia afzelii P12 for IgG and IgM, respectively; 161 (36%) and 94 (21%) individuals responded to Borrelia garinii Fuji P1 for IgG and IgM, respectively; 158 (35%) and 120 (27%) individuals responded to *Borrelia burgdorferi* sensu stricto B31 round body for IgG and IgM, respectively; 164 (37%) and 98 (22%) individuals responded to *Borrelia afzeffi* p12 round body in IgG and IgM, respectively; and, 180 (41%) and 83 (19%) individuals responded to *Borrelia garinii* Fuji P12 round body for IgG and IgM, respectively.

In FIGS. 4 and 5 immune responses to antigens apart from *Borrelia* spirochetes/round Bodies suggests that it is imperative to test individuals for secondary, co-infection and auto-immune conditions. The immune responses against IgG and IgM are as following: 125 (28%) and 59 (13%) individuals responded to *Bartonella henselae,* respectively; 126 (28%) and 74 (16%) individuals responded to *Babesia microti,* respectively; 115 (26%) and 65 (15%) individuals responded to *Chlamydia trachomatis,* respectively; 115 (26%) individuals responded to *Chlamydia pneumonia,* respectively; 167 (38%) and 122 (28%) individuals responded to *Mycoplasma fermentans,* respectively; 137 (31%) and 58 (13%) individuals responded to *Mycoplasma pneumonia,* respectively; 115 (26%) and 76 (17%) individuals responded to Coxsachie virus A16, respectively; 150 (34%) and 127 (29%) individuals responded to Cytomegalo virus, respectively; 203 (46%) and 68 (15%) individuals responded to Epstein-barr virus, respectively; 122 (28%) and 64 (14%) individuals responded to Brucella abortus, respectively; 134 (30%) and 104 (23%) individuals responded to Parvovirus B19 Apobods, respectively; 142 (32%) and 77 (17%) individuals responded to *Ehrlichia chaffeensis,* respectively; 149 (34%) and 71 (16%) individuals responded to Tick-borne encephalitis virus, respectively; 184 (47%) and 146 (33%) individuals responded to *Rickketsia akari,* respectively; and , 36 (8%) and 153 (35%) individuals did not responded to any of the 20 antigens, respectively.

FIGS. 6A, 6B, 6C, 7A, 7B and 7C demonstrate differences in immune responses by 443 individuals to other microbes with *Borrelia* spirochetes, *Borrelia* round bodies, or a combination of *Borrelia* spirochetes and round bodies and without *Borrelia*. Essentially, FIGS. 6A, 6B, 6C, 7A, 7B and 7C illustrate the differences in immune response frequencies to the number of multiple other microbes and specifically to each other microbe with and without *Borrelia* round bodies. It was observed that individuals responding to a combination of *Borrelia* spirochetes and round bodies tend to respond more not only to the number of multiple other microbes, but also to specific other microbe FIGS. 6A, 6B, 6C, 7A, 7B and 7C suggest that a diagnostic tool with *Borrelia* spirochete, *Borrelia* round body, co-infectious, secondary infections and autoimmune antigens would provide individuals a complete and reliable diagnosis for TBDs. The term "other microbes" includes co-infections, secondary and auto-immune antigens such as, but not limited to *Bartonella henselae* (*B.henselae*), *Brucella abortus* (*B. abortus*), *Babesia microti* (*B. microti*), *Ehrlichia chaffeensis* (*E. chaffeensis*), *Rickettsia akari* (*R. akari*), Tick borne encephaltis virus (TBEV), *Chlamydia trachomatis* (*C. trachomatis*), *Chlamydia pneumonia* (*C. pneumonia*), *Mycoplasma fermentans* (*M. fermentans*), *Mycoplasma pneumonia* (*M. pneumonia*), Cytomegalo virus (CMV), Epstein-barr virus (EBV), Coxsachie virus A16 (CV A16), and Human Parvovirus B19 (HB19V).

In FIGS. 6A and 7A, approximately a quarter (26%) of 443 individuals responded to other microbes without *Borrelia*. IgM and IgG immune responses from 115 (26%) and 118 (26%) individuals to other microbes without *Borrelia* suggests that individuals should also be screened for microbes other than *Borrelia*. Furthermore, FIGS. 6A and 7A present immune responses by individuals to only *Borrelia* and other microbes with *Borrelia*. It was observed that the number of individuals responding to other microbes with *Borrelia* was considerably higher when compared with the number of individuals that responded to only *Borrelia* antigens. In FIG. 6A, from the 443 individuals 10 (2%), 2 (1%), and 5 (1%) individuals responded to *Borrelia* round bodies, *Borrelia* spirochetes, and a combination of *Borrelia* spirochetes and round bodies, respectively. However, of the 443 individuals 55 (12%), 13 (3%), and 90 (20%) individuals responded to *Borrelia* round bodies, *Borrelia* spirochetes, and a combination of *Borrelia* spirochetes and round bodies with other microbes, respectively. Similarly, in FIG. 7A, of the 443 individuals 23 (5%), 2 (1%), and 13 (3%) individuals responded to *Borrelia* round bodies, *Borrelia* spirochetes, and a combination of *Borrelia* spirochetes and round bodies, respectively. But, of the 443 individuals 48 (11%), 45 (10%), and 158 (36%) individuals responded to *Borrelia* round bodies, *Borrelia* spirochetes, and a combination of *Borrelia* spirochetes and round bodies with other microbes, respectively.

In FIGS. 6A and 7A, individuals that respond to *Borrelia* round bodies tend to respond more to other microbes when compared with individuals that respond to the *Borrelia* spirochete. However, individuals that respond to a combination of *Borrelia* spirochetes and round bodies tend to respond approximately 3 fold higher to other microbes when compared with individuals that respond to *Borrelia* Round Bodies or *Borrelia* spirochetes. With IgM (FIG. 6A), the number of individuals responding to other microbes with *Borrelia* round bodies is approximately 4 fold greater when comapred with the number of individuals responding to other microbes with *Borrelia* spirochetes. But, with IgG (FIG. 7A) the number of individuals responding to other microbes with *Borrelia* round bodies is marginally similar to the number of individuals responding to other microbes with *Borrelia* spirochetes. From the 443 individuals, 55 (12%) individuals responded to other microbes with *Borrelia round bodies, whereas* 13 (3%) individuals responded to other microbes with *Borrelia* spirochete in IgM (FIG. 6A). Similarly, 48 (11%) individuals responded to other microbes with *Borrelia* round bodies and 45 (10%) individuals responded to other microbes with *Borrelia* spirochetes.

FIGS. 6B and 7B present the difference in micobial load with individuals that responded to other microbes with and without *Borrelia*. At the outset, individuals that responded to other microbes (FIGS. 6A and 7A) did not respond to more than eight microbes in both antibody classes (FIGS. 6B and 7B). However, over 75% individuals that responded to other microbes did not respond to more than three micobes. Of the 115 (26%) individuals that responded to other microbes with IgM (FIG. 6A), 92 (80%) individuals did not respond to more than three microbes. Similarly, of the 118 (26%) individuals that responded to other microbes with IgG (FIG. 7A), 89 (75%) individuals did not respond to more than three microbes. Interestingly, individuals that responded to *Borrelia* tend to respond more to multiple other microbes when compared with individuals without any response to *Borrelia* (FIGS. 6B and 7B).

Individuals that responded to *Borrelia* round bodies with IgM tend to respond more to multiple other microbes when compared with individuals that respond to *Borrelia* spirochetes (FIG. 6B). On the contrary, individuals that responded to *Borrelia* spirochetes with IgG tend to respond more to multiple other microbes when compared with individuals that respond to *Borrelia* round bodies (FIG. 7B). But, individuals responding to a combination of *Borrelia* spirochetes and round bodies consistently tend to respond higher to multiple microbes when compared either to individuals that responded to *Borrelia* round bodies or *Borrelia* spirochetes. Over 50% individuals that responded to other microbes with a combination of *Borrelia* spirochetes and round bodies, responded from 8 to 14 multiple other microbes. Concentration of individuals that responded to other microbes with a combination of *Borrelia* spirochetes and round bodies is the highest at 14 multiple microbes in both antibody classes (FIGS. 6B and 7B). Of the 90 (20%) individuals that responded to other microbes with IgM to a combination of *Borrelia* spirochetes and round bodies (FIG. 6A), 14 (16%) individuals responded to 14 other microbes (FIG. 6B). Similarly, of the 158 (36%) individuals that responded to other microbes with IgG to a combination of *Borrelia* spirochetes and round bodies (FIG. 7A), 23 (15%) individuals responded to 14 other microbes (FIG. 7B).

FIGS. 6C and 7C demonstrate differences in immune responses from 443 individuals to individual other microbes with and without *Borrelia*. *Borrelia* antigens that exhibited the greatest amount of microbial load in FIGS. 6B and 7B also presented highest frequency of immune responses to individual other microbes in FIGS. 6C and 7C. From FIGS. 6B and 7B, *Borrelia* round bodies and *Borrelia* spirochetes exhibited the most microbial load in individuals with IgM and IgG, respectively. Thus, individuals that responded to *Borrelia* round bodies with IgM responded on average 5 fold higher to all other microbes when compared with individuals that responded to *Borrelia* spirochetes (FIG. 6C). Furthermore, individuals that responded to *Borrelia* spirochete with IgG responded on an average 2 fold higher to all other microbes when compared with individuals that responded to *Borrelia* round bodies (FIG. 7C). However, combination of *Borrelia* spirochetes and round bodies exhibited the greatest amount of microbial load in both antibody classes (FIGS. 6B and 7B). Thus, individuals that responded to a combination of *Borrelia* spirochetes and round bodies with IgM responded approximately 3 fold higher to all other microbes when compared with individuals that responded to *Borrelia* round bodies (FIG. 6C). Also, individuals that responded to a combination of *Borrelia* spirochetes and Round Bodies with IgG responded about 5 fold higher to all other microbes when compared with individuals that responded to *Borrelia* spirochetes (FIG. 7C).

Intra and Inter Assay Variation

The Intra and inter assay variation for the present method was calculated to be 4.6% and 15.6%, respectively.

TABLE 1

List of 20 tick-borne microbial antigens utilized in the present method.

| Microbial antigens | Antigen types | Culturing/Peptide Sequences | Ref. |
|---|---|---|---|
| *Borrelia burgdorferi sensu stricto* B31 | Full lysate | Previously reported | 14 |
| *Borrelia afzelii* P12 | Full lysate (ATCC 51567) | Previously reported | |
| *Borrelia garinii* Fuji P1 | Full lysate (ATCC 51991) | Previously reported | |
| *Borrelia burgdorferi sensu stricto* B31 round body | Full lysate (ATCC35210) | Previously reported | |
| *Borrelia afzelii* P12 round body | Full lysate (ATCC 51567) | Previous reported | |
| *Borrelia garinii* Fuji P1 round body | Full lysate (ATCC 51991) | Previously reported | |
| *Chlamydia trachomatis* | Peptide | Seq 1: MIFDTTLNPTIAGAGDV (SEQ ID NO: 1)<br>Seq 2: MLAEAILDVTLNPTIGKAVVSK (SEQ ID NO: 2) | 28 |
| *Chlamydia pneumonia* | Peptide | Seq 1: CFGVKGTTVNANEL (SEQ ID NO: 3)<br>Seq 2: CQINKFKSRKAC (SEQ ID NO: 4) | 29 |
| *Mycoplasma fermentans* | Peptide | Seq 1: MNKKFLKLGSIAGILSFAPVAISAGC (SEQ ID NO: 5)<br>Seq 2: FKLAKFENNKPVLDDPIVYNAEVSLA (SEQ ID NO: 6) | 30 |
| *Mycoplasma pneumonia* | Peptide | Seq 1: WIGNGYRY (SEQ ID NO: 7)<br>Seq 2: FTDFVKPR (SEQ ID NO: 8) | 31 |
| *Bartonella henselae* | Peptide | EDLQKQLKEKLEKSDVRL (SEQ ID NO: 9) | 32 |

TABLE 1-continued

List of 20 tick-borne microbial antigens utilized in the present method.

| Microbial antigens | Antigen types | Culturing/Peptide Sequences | Ref. |
|---|---|---|---|
| *Brucella abortus* | Peptide | TTSLKTF (SEQ ID NO: 10) | 33 |
| *Babesia microti* | Peptide | IVEFNAIFSNIDLNNSSTVKNEIIK (SEQ ID NO: 11) | 34 |
| *Ehrlichia chaffeensis* | Peptide | SAVSNRKLPLGGVLMALVAAVAPIHSALLA (SEQ ID NO: 12) | |
| *Coxsackie virus* A16 | Peptide | YLFKTNPNYKGNDIK (SEQ ID NO: 13) | 35 |
| *Epstein-barr virus* | Peptide | Seq 1: AVDTGSGGGGQPHDTAPRGARKKQ (SEQ ID NO: 14)<br>Seq 2: STAVAQSATPSVSSSISSLRAATSGATAAA (SEQ ID NO: 15) | 36 |
| *Cytomegalo virus* | Peptide | KSGTGPQPGSAGMGGAKTPSDAVQNILQKIEKIKNTEE (SEQ ID NO:16) | 37 |
| Human Parvovirus B19 Apobods | Peptide | Previously reported | 26, 27 |
| Tick-borne encephalitis virus | Peptide | Seq 1: SRCTHLENRDFVTGTQGTTRVT (SEQ ID NO: 17)<br>Seq 2: NDLALPWKHEGAQNWNNAERC (SEQ ID NO: 18) | 38 |
| *Rickettsia akari* | Full Lysate | Provided by Dr. Marco Quvendi Diaz, Slovakia | |

REFERENCES

1. Steere A C, Coburn J, Glickstein L. The emergence of Lyme disease. J Clin Invest. 2004 Apr. 4; 113(8):1093-101.
2. Steere A C. Lyme disease. N Engl J Med. 2001 Jul. 4; 345(2):115-25.
3. Chomel B. Lyme disease. Rev-Off Int Epizoot. 2015 Aug. 6; 34(2):569-76.
4. Mead P S. Epidemiology of Lyme disease. Infect Dis Clin North Am. 2015 Jun. 1; 29(2):187-210.
5. Stricker R B, Johnson L. Lyme disease: the next decade. Infect Drug Resist. 2011 Jan. 6; 4:1-9.
6. Berghoff W. Chronic Lyme Disease and Co-infections: Differential Diagnosis. Open Neurol J. 2012 January; 6:158-78.
7. Lindgren E, Jaenson T G T. Lyme borreliosis in Europe: influences of climate and climate change, epidemiology, ecology and adaptation measures. WHO Regional Office for Europe. WHO Regional Office for Europe; 2006; EUR/04 (/5046250):34.
8. Donta S. Issues in the Diagnosis and Treatment of Lyme Disease. Open Neurology J. bentham; 2012; 6(1):140-5.
9. Johnson L, Wilcox S, Mankoff J, Stricker R B. Severity of chronic Lyme disease compared to other chronic conditions: a quality of life survey. PeerJ. 2014 Jan. 3; 2:e322.
10. Adrion E R, Aucott J, Lemke K W, Weiner J P. Health care costs, utilization and patterns of care following Lyme disease. PLoS ONE. 2015 Jan. 4; 10(2):e0116767.
11. Wilske B. Epidemiology and diagnosis of Lyme borreliosis. Ann Med. 2005 Jan. 6; 37(8):568-79.
12. Brogden K A, Guthmiller J M, Taylor C E. Human polymicrobial infections. Lancet. 2005 Jan. 6; 365(9455): 253-5.
13. Aguero-Rosenfeld M, Wang G, Schwartz I, Wormser G. Diagnosis of Lyme Borreliosis. Clin Microbiol Rev. highwire; 2005; 18(3):484-509.
14. Meriläinen L, Herranen A, Schwarzbach A, Gilbert L. Morphological and biochemical features of *Borrelia burgdorferi* pleomorphic forms. Microbiology (Reading, Engl). 2015 March; 161(Pt 3):516-27.
15. Seinost G, Golde W T, Berger B W, Dunn J J, Qiu D, Dunkin D S, et al. Infection with multiple strains of *Borrelia burgdorferi* sensu stricto in patients with Lyme disease. Arch Dermatol. 1999 Nov. 1; 135(11):1329-33.
16. Dhote R, Basse-Guerineau A L, Bachmeyer C, Christoforov B, Assous M V. [Lyme borreliosis: therapeutic aspects]. Presse Med. 1998 Dec. 6; 27(39):2043-7.
17. Kalish, McHugh, Granquist, Shea, Ruthazer, Steere. Persistence of immunoglobulin M or immunoglobulin G antibody responses to *Borrelia burgdorferi* 10-20 years after active Lyme disease. Clin Infect Dis Official Publ Infect Dis Soc Am. highwire; 2001; 33(6):780-5.
18. Mursic V P, Wanner G, Reinhardt S, Wilske B, Busch U, Marget W. Formation and cultivation of *Borrelia burgdorferi* spheroplast-L-form variants. Infection. 1996 Jan. 1; 24(3):218-26.
19. Domingue, Woody. Bacterial persistence and expression of disease. Clin Microbiol Rev. 1997; 10(2):320-44.
20. Murgia R, Piazzetta C, Cinco M. Cystic forms of *Borrelia burgdorferi* sensu lato: induction, development, and the role of RpoS. Wien Klin Wochenschr. 2002 Jul. 3; 114(13-14):574-9.

21. Schenk J, Doebis C, Küsters U, von Baehr V. Evaluation of a New Multiparametric Microspot Array for Serodiagnosis of Lyme Borreliosis. Clin Lab. 2015 Jan. 4; 61(11):1715-25.

22. Lahey L J, Panas M W, Mao R, Delanoy M, Flanagan J J, Binder S R, et al. Development of a Multiantigen Panel for Improved Detection of *Borrelia burgdorferi* Infection in Early Lyme Disease. J Clin Microbiol. 2015 Dec. 2; 53(12): 3834-41.

23. Embers M E, Hasenkampf N R, Barnes M B, Didier E S, Philipp M T, Tardo A C. A Five-Antigen Fluorescent Bead-based Assay for Diagnosis of Lyme Disease. Clin Vaccine Immunol. 2016 Feb. 3.

24. Porwancher R B, Hagerty C G, Fan J, Landsberg L, Johnson B J, Kopnitsky M, et al. Multiplex immunoassay for Lyme disease using VIsE1-IgG and pepC10-IgM antibodies: improving test performance through bioinformatics. Clin Vaccine Immunol. 2011 May; 18(5):851-9.

25. Dessau R B, Moller J K, Kolmos B, Henningsson A J. Multiplex assay (Mikrogen recomBead) for detection of serum IgG and IgM antibodies to 13 recombinant antigens of *Borrelia burgdorferi* sensu lato in patients with neuroborreliosis: the more the better? J Med Microbiol. 2015 March; 64(Pt 3):224-31.

26. Kivovich V, Gilbert L, Vuento M, Naides S J. Parvovirus B19 genotype specific amino acid substitution in NS1 reduces the protein's cytotoxicity in culture. Int J Med Sci. 2010 Jan. 5; 7(3)110-9.

27. Thammasri K, Rauhamäki S, Wang L, Filippou A, Kivovich V, Marjomäki V, et al. Human parvovirus B19 induced apoptotic bodies contain altered self-antigens that are phagocytosed by antigen presenting cells. PLoS ONE. 2013 Jan. 2; 8(6):e67179.

28. U.S. Pat. No. 6,699,678 B1,*Chlamydia trachomatis* specific peptides and their use in diagnostic assays. United States Patent.

29. Mitchell W M, Stratton C W. Diagnosis and management of infection caused by chlamydia. United States Patent; U.S. Pat. No. 6,579,854 B1, 1998.

30. Theiss P, Karpas A, Wise K S. Antigenic topology of the P29 surface lipoprotein of *Mycoplasma fermentans*: differential display of epitopes results in high-frequency phase variation. Infect Immun. 1996 May 3; 64(5):1800-9.

31. Jacobs E, Pilatschek A, Gerstenecker B, Oberle K, Bredt W. Immunodominant epitopes of the adhesin of *Mycoplasma pneumoniae*. J Clin Microbiol. 1990 Jun. 5; 28(6): 1194-7.

32. Huang L, Hoey J, Adelson M, Mordechai E. Recombinant fragments and synthetic peptides of 17-kda polypeptide useful in detecting *Bartonella henselae*. European Patent; EP2326660 A2, 2011.

33. Zhang J, Guo F, Huang X, Chen C, Liu R, Zhang H, et al. A novel Omp25-binding peptide screened by phage display can inhibit Brucella abortus 2308 infection in vitro and in vivo. J Med Microbiol. 2014 June; 63(Pt 6):780-7.

34. Flores O, Schwarzch A, Rredo B, Altieri G U. Biochip, antigen bouquet, optical reader and method for detecting and monitoring diseases. WIPO; WO2014185803 A2, 2014.

35. Shi J, Huang X, Liu Q, Huang Z. Identification of conserved neutralizing linear epitopes within the VP1 protein of coxsackievirus Al 6. Vaccine. 2013 Apr. 5; 31(17): 2130-6.

36. Middeldorp J M, van Grunsven W M J. Peptides and nucleic acid sequences related to the Epstein Barr virus. United States Patent; U.S. Pat. No. 7,507,804 B2, 2009.

37. Landini M P, Ripalti A, Sra K, Pouletty P. Human cytomegalovirus structural proteins: immune reaction against pp150 synthetic peptides. J Clin Microbiol. 1991 September; 29(9):1868-72.

38. Holzmann H, Utter G, Norrby E, Mandl C W, Kunz C, Heinz F X. Assessment of the antigenic structure of tick-borne encephalitis virus by the use of synthetic peptides. J Gen Virol. 1993 Sep. 3; 74 (Pt 9):2031-5.

39. Barbour A G, Hayes S F. Biology of *Borrelia* species. Microbiol Rev. 1986 Dec 1; 50(4):381-400.

40. Dudal S, Baltrukonis D, Crisino R, Goyal M J, Joyce A, Osterlund K, et al. Assay formats: Recommendation for best practices and harmonization from the global bioanalysis consortium harmonization team. AAPS J. 2014 Mar. 6; 16(2):194-205.

41. Puttaraksa K, Meriläinen L, Capillo A, Schwarzbach A, garcia P, Gilbert L. Indirect ELISA diagnostic test for Lyme Disease. Jyväskylä; 2015.

42. Reed G F, Lynn F, Meade B D. Use of coefficient of variation in assessing variability of quantitative assays. Clin Diagn Lab Immunol. 2002 Nov. 5; 9(6):1235-9.

43. Shoberg R J, Jonsson M, Sadziene A, Bergström S, Thomas D D. Identification of a highly cross-reactive outer surface protein B epitope among diverse geographic isolates of *Borrelia* spp. causing Lyme disease. J Clin Microbiol. 1994 Feb. 2; 32(2):489-500.

44. Wormser G P, Liveris D, Hanincová K, Brisson D, Ludin S, Stracuzzi V J, et al. Effect of *Borrelia burgdorferi* genotype on the sensitivity of C6 and 2-tier testing in North American patients with culture-confirmed Lyme disease. Clin Infect Dis. 2008 Oct. 3; 47(7):910-4.

45. O'Connor S M M, Taylor C E, Hughes J M. Emerging infectious determinants of chronic diseases. Emerging Infect Dis. 2006 Jul. 6; 12(7):1051-7.

46. Wormser G P, Dattwyler R J, Shapiro E D, Halperin J J, Steere A C, Klempner M S, et al. The clinical assessment, treatment, and prevention of lyme disease, human granulocytic anaplasmosis, and babesiosis: clinical practice guidelines by the Infectious Diseases Society of America. Clin Infect Dis. 2006 Nov. 3; 43(9)1 089-134.

47. Miklossy, J., Kasas, S., Zurn, A., McCall, S., Yu, S., and McGeer. Persisting atypical and cystic forms of *Borrelia burgdorferi* and local inflammation in Lyme neuroborreliosis. J Neuroinflammation. Journal of Neuroinflammation, 2008, 5:40.

48. Cook, Michael J. Lyme borreliosis: a review of data on transmission time after tick attachment. International Journal of General Medicine, 2015, 8:1-8

The invention claimed is:

1. A solid support for detecting the presence of antibodies in a biological sample, said solid support comprising microbial antigens immobilized on said solid support, wherein said microbial antigens comprise antigens specific to lysates of pleomorphic round bodies of *Borrelia burgdorferi, Borrelia afzelii* and *Borrelia garinii.*

2. The solid support according to claim 1, wherein said solid support is a microwell plate or antigen microarray.

3. The solid support according to claim 1, wherein said solid support comprises an immobilized antigen prepared from lysates of pleomorphic round bodies of *Borrelia burgdorferi* in a native spirochete form.

4. The solid support according to claim 1, wherein said solid support comprises an immobilized antigen prepared from lysates of pleomorphic round bodies of *Borrelia afzelii* in a native spirochete form.

5. The solid support according to claim 1, wherein said solid support comprises an immobilized antigen prepared from lysates of pleomorphic round bodies of *Borrelia garinii* in a native spirochete form.

6. The solid support according to claim 1, further comprising at least one immobilized antigen prepared from the group consisting of *Mycoplasma fermentans, Mycoplasma pneumonia, Bartonella henselae, Brucella abortus, Babesia microti, Chlamydia trachomatis, Chlamydia pneumonia, Ehrlichia chaffeensis,* Coxsackie virus A16, Epstein-barr virus, Cytomegalo virus, Human Parvovirus B19 Apobods, Tick-borne encephalitis virus, and *Rickettsia akari.*

7. The solid support according to claim 1, for use in the diagnosis of Lyme disease.

8. The solid support according to claim 7, for use in the diagnosis of Lyme disease, wherein said Lyme disease is chronic or persistent Lyme disease.

* * * * *

SEQUENCE LISTING

```
<160> NUMBER OF SEQ ID NOS: 18

<210> SEQ ID NO 1
<211> LENGTH: 17
<212> TYPE: PRT
<213> ORGANISM: Chlamydia trachomatis
```

```
<400> SEQUENCE: 1

Met Ile Phe Asp Thr Thr Leu Asn Pro Thr Ile Ala Gly Ala Gly Asp
1               5                   10                  15

Val

<210> SEQ ID NO 2
<211> LENGTH: 22
<212> TYPE: PRT
<213> ORGANISM: Chlamydia trachomatis

<400> SEQUENCE: 2

Met Leu Ala Glu Ala Ile Leu Asp Val Thr Leu Asn Pro Thr Ile Gly
1               5                   10                  15

Lys Ala Val Val Ser Lys
            20

<210> SEQ ID NO 3
<211> LENGTH: 14
<212> TYPE: PRT
<213> ORGANISM: Chlamydia pneumoniae

<400> SEQUENCE: 3

Cys Phe Gly Val Lys Gly Thr Thr Val Asn Ala Asn Glu Leu
1               5                   10

<210> SEQ ID NO 4
<211> LENGTH: 12
<212> TYPE: PRT
<213> ORGANISM: Chlamydia pneumoniae

<400> SEQUENCE: 4

Cys Gln Ile Asn Lys Phe Lys Ser Arg Lys Ala Cys
1               5                   10

<210> SEQ ID NO 5
<211> LENGTH: 26
<212> TYPE: PRT
<213> ORGANISM: Mycoplasma fermentans

<400> SEQUENCE: 5

Met Asn Lys Lys Phe Leu Lys Leu Gly Ser Ile Ala Gly Ile Leu Ser
1               5                   10                  15

Phe Ala Pro Val Ala Ile Ser Ala Gly Cys
            20                  25

<210> SEQ ID NO 6
<211> LENGTH: 26
<212> TYPE: PRT
<213> ORGANISM: Mycoplasma fermentans

<400> SEQUENCE: 6

Phe Lys Leu Ala Lys Phe Glu Asn Asn Lys Pro Val Leu Asp Asp Pro
1               5                   10                  15

Ile Val Tyr Asn Ala Glu Val Ser Leu Ala
            20                  25

<210> SEQ ID NO 7
<211> LENGTH: 8
<212> TYPE: PRT
<213> ORGANISM: Mycoplasma pneumoniae

<400> SEQUENCE: 7
```

```
Trp Ile Gly Asn Gly Tyr Arg Tyr
1               5

<210> SEQ ID NO 8
<211> LENGTH: 8
<212> TYPE: PRT
<213> ORGANISM: Mycoplasma pneumoniae

<400> SEQUENCE: 8

Phe Thr Asp Phe Val Lys Pro Arg
1               5

<210> SEQ ID NO 9
<211> LENGTH: 18
<212> TYPE: PRT
<213> ORGANISM: Bartonella henselae

<400> SEQUENCE: 9

Glu Asp Leu Gln Lys Gln Leu Lys Glu Lys Leu Glu Lys Ser Asp Val
1               5                   10                  15

Arg Leu

<210> SEQ ID NO 10
<211> LENGTH: 7
<212> TYPE: PRT
<213> ORGANISM: Brucella abortus

<400> SEQUENCE: 10

Thr Thr Ser Leu Lys Thr Phe
1               5

<210> SEQ ID NO 11
<211> LENGTH: 25
<212> TYPE: PRT
<213> ORGANISM: Babesia microti

<400> SEQUENCE: 11

Ile Val Glu Phe Asn Ala Ile Phe Ser Asn Ile Asp Leu Asn Asn Ser
1               5                   10                  15

Ser Thr Val Lys Asn Glu Ile Ile Lys
            20                  25

<210> SEQ ID NO 12
<211> LENGTH: 30
<212> TYPE: PRT
<213> ORGANISM: Ehrlichia chaffeensis

<400> SEQUENCE: 12

Ser Ala Val Ser Asn Arg Lys Leu Pro Leu Gly Gly Val Leu Met Ala
1               5                   10                  15

Leu Val Ala Ala Val Ala Pro Ile His Ser Ala Leu Leu Ala
            20                  25                  30

<210> SEQ ID NO 13
<211> LENGTH: 15
<212> TYPE: PRT
<213> ORGANISM: Human coxsackievirus A16

<400> SEQUENCE: 13

Tyr Leu Phe Lys Thr Asn Pro Asn Tyr Lys Gly Asn Asp Ile Lys
1               5                   10                  15
```

```
<210> SEQ ID NO 14
<211> LENGTH: 24
<212> TYPE: PRT
<213> ORGANISM: Human herpesvirus 4

<400> SEQUENCE: 14

Ala Val Asp Thr Gly Ser Gly Gly Gly Gln Pro His Asp Thr Ala
1               5                   10                  15

Pro Arg Gly Ala Arg Lys Lys Gln
            20

<210> SEQ ID NO 15
<211> LENGTH: 30
<212> TYPE: PRT
<213> ORGANISM: Human herpesvirus 4

<400> SEQUENCE: 15

Ser Thr Ala Val Ala Gln Ser Ala Thr Pro Ser Val Ser Ser Ser Ile
1               5                   10                  15

Ser Ser Leu Arg Ala Ala Thr Ser Gly Ala Thr Ala Ala Ala
            20                  25                  30

<210> SEQ ID NO 16
<211> LENGTH: 38
<212> TYPE: PRT
<213> ORGANISM: Cytomegalovirus

<400> SEQUENCE: 16

Lys Ser Gly Thr Gly Pro Gln Pro Gly Ser Ala Gly Met Gly Gly Ala
1               5                   10                  15

Lys Thr Pro Ser Asp Ala Val Gln Asn Ile Leu Gln Lys Ile Glu Lys
            20                  25                  30

Ile Lys Asn Thr Glu Glu
        35

<210> SEQ ID NO 17
<211> LENGTH: 22
<212> TYPE: PRT
<213> ORGANISM: Tick-borne encephalitis virus

<400> SEQUENCE: 17

Ser Arg Cys Thr His Leu Glu Asn Arg Asp Phe Val Thr Gly Thr Gln
1               5                   10                  15

Gly Thr Thr Arg Val Thr
            20

<210> SEQ ID NO 18
<211> LENGTH: 21
<212> TYPE: PRT
<213> ORGANISM: Tick-borne encephalitis virus

<400> SEQUENCE: 18

Asn Asp Leu Ala Leu Pro Trp Lys His Glu Gly Ala Gln Asn Trp Asn
1               5                   10                  15

Asn Ala Glu Arg Cys
        20
```